United States Patent
Zehavi et al.

(10) Patent No.: US 12,171,470 B2
(45) Date of Patent: Dec. 24, 2024

(54) SURGICAL FIXATION SYSTEMS, METHODS, AND DEVICES

(71) Applicant: MAZOR ROBOTICS LTD., Caesarea (IL)

(72) Inventors: Eli Zehavi, Haifa (IL); Yonatan Ushpizin, Glil Yam (IL); Aviv Ellman, Kfar Sava (IL); Dany Junio, Tel Aviv-Jaffa (IL); Elad Ratzabi, Ramat Gan (IL); Yair Schwartz, Raanana (IL); Yuval Chen, Tel Aviv-Jaffa (IL)

(73) Assignee: MAZOR ROBOTICS LTD., Caesarea (IL)

( * ) Notice: Subject to any disclaimer, the term of this patent is extended or adjusted under 35 U.S.C. 154(b) by 751 days.

(21) Appl. No.: 16/944,553

(22) Filed: Jul. 31, 2020

(65) Prior Publication Data

US 2022/0031370 A1 Feb. 3, 2022

(51) Int. Cl.
 *A61B 17/70* (2006.01)
 *A61B 34/20* (2016.01)
 (Continued)

(52) U.S. Cl.
 CPC ...... *A61B 17/7076* (2013.01); *A61B 17/7062* (2013.01); *A61B 34/20* (2016.02);
 (Continued)

(58) Field of Classification Search
 CPC . A61B 17/7076; A61B 17/7062; A61B 34/20; A61B 90/39; A61B 90/57;
 (Continued)

(56) References Cited

U.S. PATENT DOCUMENTS

| 5,147,359 A | 9/1992 | Cozad et al. |
| 5,984,923 A | 11/1999 | Breard |

(Continued)

FOREIGN PATENT DOCUMENTS

| DE | 102014200513 | 7/2015 |
| EP | 1278468 | 10/2005 |

(Continued)

OTHER PUBLICATIONS

International Search Report and Written Opinion for International (PCT) Patent Application No. PCT/IL2021/050916, dated Jan. 27, 2022, 21 pages.

(Continued)

*Primary Examiner* — Nicholas J Plionis
(74) *Attorney, Agent, or Firm* — Sheridan Ross P.C.

(57) ABSTRACT

A spinal stabilization system includes a plurality of anchors and at least one bridge. Each anchor includes a clamp configured to engage an anatomical element, the clamp movable between a fully open position and a fully closed position; a locking screw configured to selectively prevent the clamp from being moved into the fully open position; and a bridge interface. The at least one bridge is a rigid member having a first end and a second end opposite the first end, each of the first end and the second end having an anchor interface. The bridge interface is configured to receive the anchor interface.

18 Claims, 5 Drawing Sheets

(51) Int. Cl.
*A61B 90/00* (2016.01)
*A61B 90/57* (2016.01)

(52) U.S. Cl.
CPC .............. *A61B 90/39* (2016.02); *A61B 90/57* (2016.02); *A61B 2034/2051* (2016.02); *A61B 2034/2055* (2016.02); *A61B 2090/397* (2016.02); *A61B 2090/571* (2016.02)

(58) Field of Classification Search
CPC .... A61B 2034/2051; A61B 2034/2055; A61B 2090/397; A61B 2090/571
See application file for complete search history.

(56) References Cited

U.S. PATENT DOCUMENTS

| | | |
|---|---|---|
| 6,802,844 B2 | 10/2004 | Ferree |
| 7,686,833 B1 | 3/2010 | Muhanna et al. |
| 7,846,186 B2 | 12/2010 | Taylor |
| 7,985,245 B2 | 7/2011 | Ritland |
| RE42,626 E | 8/2011 | Taylor et al. |
| 8,313,515 B2 | 11/2012 | Brennan et al. |
| 8,317,838 B2 | 11/2012 | Nguyen et al. |
| 8,449,577 B2 | 5/2013 | Kloss et al. |
| 8,551,142 B2 | 10/2013 | Altarac et al. |
| 8,617,216 B2 | 12/2013 | Brumfield |
| 8,900,273 B2 | 12/2014 | Fauth et al. |
| 9,138,277 B2 | 9/2015 | Fitzpatrick |
| 9,987,024 B2 | 6/2018 | Frey et al. |
| 10,098,667 B2 | 10/2018 | Larroque-Lahitette et al. |
| 10,231,759 B2 | 3/2019 | Heigl et al. |
| 10,321,936 B2 | 6/2019 | Backes |
| 10,405,935 B2 | 9/2019 | McGahan et al. |
| 2005/0240188 A1* | 10/2005 | Chow .................. A61B 17/683 606/86 R |
| 2007/0100346 A1 | 5/2007 | Wyss et al. |
| 2007/0161994 A1 | 7/2007 | Lowery et al. |
| 2008/0097441 A1* | 4/2008 | Hayes ................. A61B 17/7025 606/151 |
| 2010/0249846 A1 | 9/2010 | Simonson |
| 2011/0178552 A1 | 7/2011 | Biscup et al. |
| 2011/0251648 A1 | 10/2011 | Fiechter et al. |
| 2012/0041490 A1 | 2/2012 | Jacob et al. |
| 2012/0253400 A1 | 10/2012 | Clark et al. |
| 2013/0072979 A1* | 3/2013 | Butler ................. A61B 17/7067 606/248 |
| 2013/0090692 A1 | 4/2013 | Nuckley et al. |
| 2014/0046191 A1* | 2/2014 | Anker .................. A61B 5/1127 600/407 |
| 2014/0222078 A1* | 8/2014 | Triplett ............... A61B 17/7004 606/265 |
| 2016/0183981 A1 | 6/2016 | Schlaepfer et al. |
| 2017/0181772 A1* | 6/2017 | Buttermann ........ A61B 17/7056 |
| 2017/0348061 A1* | 12/2017 | Joshi ...................... A61B 90/90 |
| 2020/0170682 A1* | 6/2020 | Boehm, Jr. ......... A61B 17/7062 |

FOREIGN PATENT DOCUMENTS

| | | |
|---|---|---|
| EP | 2911599 | 4/2020 |
| KR | 10-2009-0080411 | 7/2009 |
| KR | 10-0963266 | 6/2010 |
| WO | WO 2020/033589 | 2/2020 |
| WO | WO 2020/079598 | 4/2020 |

OTHER PUBLICATIONS

U.S. Appl. No. 63/044,535, filed Jun. 26, 2020.

* cited by examiner

SURGICAL FIXATION SYSTEMS, METHODS, AND DEVICES

FIELD

The present technology is generally related to surgical hardware, and is more specifically related to hardware for preventing movement of a patient during a surgical procedure.

BACKGROUND

During a surgical procedure, a patient is often positioned on an operating table or in a chair. Whether due to normal bodily functions (including voluntary and involuntary processes and/or reactions) or external stimuli such as surgical intervention, one or more anatomical features of the patient may move relative to the operating table or chair, relative to another external reference, and/or relative to another anatomical feature.

Surgical procedures may involve the use any number of surgical tools, including tools configured for cutting, grinding, roughing, cleaning, and otherwise interacting with soft and/or hard tissue, as well as tools configured for use with implant insertion. Such tools may be, for example, held and manipulated by a surgeon, held by a passive mechanical fixture or a robotic arm while being manipulated by a surgeon, held and manipulated by a robotic arm controlled by a surgeon, or held and manipulated by a robotic arm under autonomous control.

SUMMARY

Example aspects of the present disclosure:

A spinal stabilization system, comprising: a plurality of anchors; and at least one bridge comprising a rigid member having a first end and a second end opposite the first end, each of the first end and the second end comprising an anchor interface. Each anchor comprises: a clamp configured to engage an anatomical element, the clamp movable between a fully open position and a fully closed position; a locking screw configured to selectively prevent the clamp from being moved into the fully open position; and a bridge interface. The bridge interface is configured to receive the anchor interface.

Any of the aspects herein, wherein a first one of the plurality of anchors has a first height, and a second one of the plurality of anchors has a second height different than the first height.

Any of the aspects herein, wherein a first one of the plurality of anchors has a first height less than 10 cm, and a second one of the plurality of anchors has a second height greater than or equal to 10 cm.

Any of the aspects herein, wherein each anchor further comprises a spring that biases the clamp toward the fully closed position.

Any of the aspects herein, wherein the clamp comprises: a first contact surface opposite and facing a second contact surface; and a plurality of teeth on at least one of the first contact surface and the second contact surface, the plurality of teeth configured to prevent movement of the clamp relative to the anatomical element when the clamp is engaged with the anatomical element.

Any of the aspects herein, wherein one of the bridge interface and the anchor interface is a ball, and the other of the bridge interface and the anchor interface is a socket.

Any of the aspects herein, wherein the bridge interface further comprises a lock configured to selectively prevent movement of the bridge relative to the anchor when the anchor interface is received by the bridge interface.

Any of the aspects herein, wherein at least one anchor of the plurality of anchors comprises a tracking marker.

Any of the aspects herein, wherein at least one anchor of the plurality of anchors comprises two bridge interfaces.

Any of the aspects herein, wherein the at least one bridge is a plurality of bridges, and a first bridge of the plurality of bridges has a first length different than a second length of a second bridge of the plurality of bridges.

An anatomical stabilization system comprising an anchor. The anchor comprises: a clamping mechanism for securing the anchor to an anatomical feature and comprising first and second contact surfaces, each having a non-slip feature; a lock configurable to prevent release of the clamping mechanism from the anatomical feature; at least one bridge receptacle; and a tracking marker.

Any of the aspects herein, further comprising: a bridge comprising a rigid elongate member with a first end opposite a second end, the first end configured to be received by the at least one bridge receptacle.

Any of the aspects herein, wherein the bridge comprises a photoelastic material.

Any of the aspects herein, further comprising a plurality of anchors and a plurality of bridges.

Any of the aspects herein, further comprising an adaptor for securing the second end of the bridge to a surgical robot, an operating table, or a bed.

Any of the aspects herein, wherein the clamping mechanism is configured to be secured to a plurality of anatomical features simultaneously.

Any of the aspects herein, wherein the tracking marker is an optical tracking marker or an electromagnetic tracking marker.

A method of tracking anatomical movement, comprising: receiving first sensor information corresponding to a first pose, at a first time, of an anchor attached to an anatomical element via a clamp, the anchor comprising a tracking marker; receiving second sensor information corresponding to a second pose, at a second time after the first time, of the anchor; determining an initial pose of the anatomical element based at least in part on the first sensor information; determining an updated pose of the anatomical element based at least in part on the second sensor information; and comparing the updated pose to the initial pose to identify movement of the anatomical element from the first time to the second time.

Any of the aspects herein, further comprising: receiving strain information corresponding to a detected strain in a bridge made of photoelastic material and fixedly secured to the anchor; and causing a strain value to be displayed on a user interface, the strain value based at least in part on the strain information.

Any of the aspects herein, wherein the tracking marker is a passive tracking marker.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
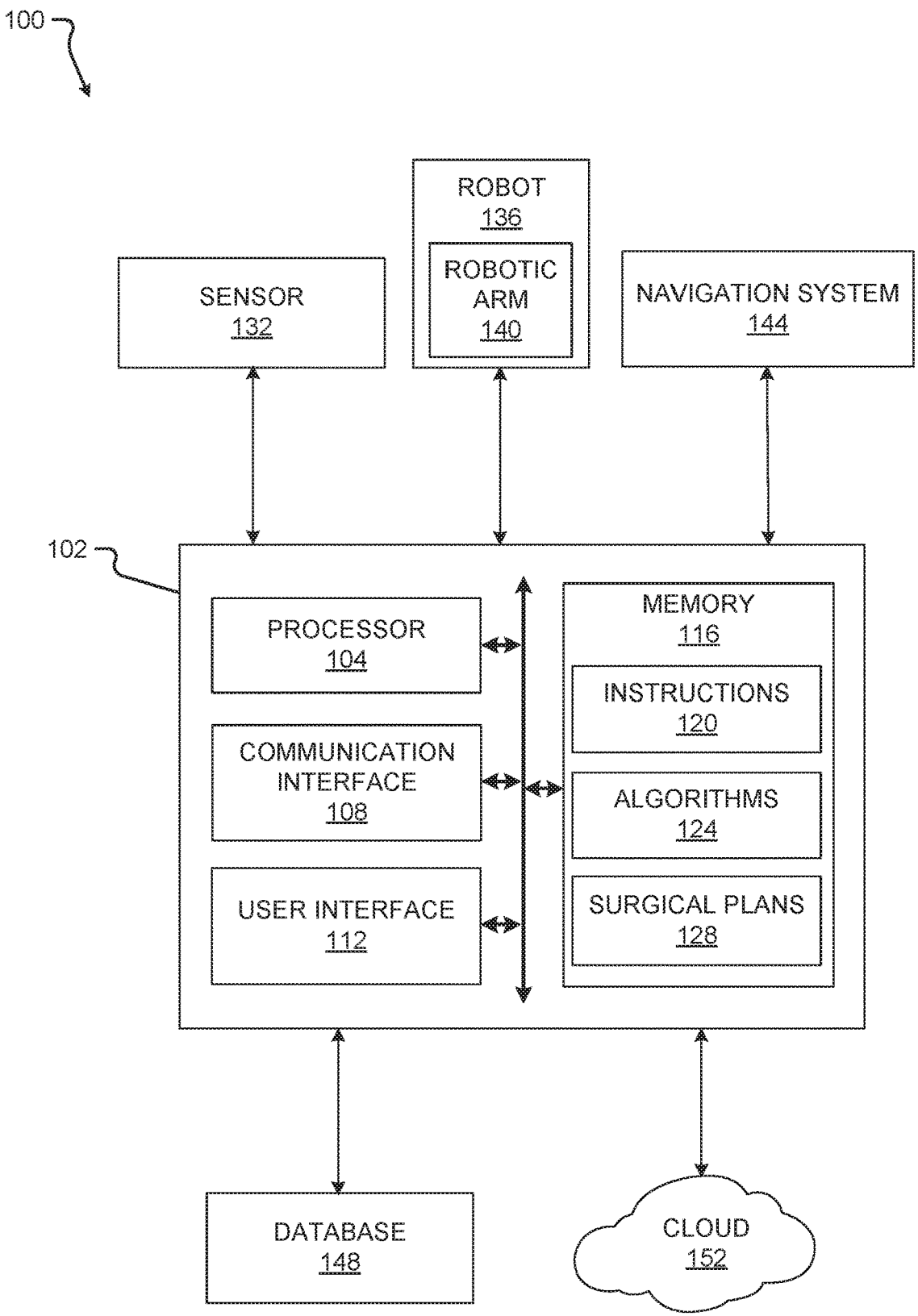
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the methods of this disclosure may be performed by a combination of units or modules associated with, for example, a computing device and/or a medical device (including a medical imaging device).

In one or more examples, one or more steps of the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure. Also, unless explicitly stated otherwise, terms such as "about" and "approximately" when used in connection with a stated value mean within ten percent of the stated value.

Embodiments of the present disclosure may be useful for any surgical procedure. Robotic and navigation system used in surgery may require patient reference or fixation systems relative to the patient's bony anatomy. During spine surgery, to take just one example, segmental motion of vertebrae may reduce guidance accuracy when using guided stereotactic systems such as robotics or navigation. (A segment is an individual bone capable of moving in relation to adjacent bones.) Such motion may result from the application of force, and may reduce guidance and/or navigation accuracy. Bone-mounted platforms or other anchors connected to the spinal anatomy and to the reference system may be used for restraining such relative motion. Bone-mounted platforms or other anchors may include spinous process clamps or pins, PSIS pins and bridge-type instruments. The reference system may include one or more navigation references and/or table mounted robotic systems.

A mechanically linked multi-anchor fixation system according to at least one embodiment of the present disclosure is directly attached to multiple bony structures, thus restraining segmental movement and reflecting the average motion of the segment of interest.

Each individual anchor may be or comprise a clamp designed for single/multiple spinal process attachment, a percutaneous pin designed for pelvic attachment, a percutaneous pin designed for spinous process attachment with or without a positive stop; and/or a fixation system designed to connect to existing hardware such as screws or rods in revision cases with previously implemented hardware.

The mechanical link between anchors may be, in some embodiments, a single radiolucent bridge or a series of small radiolucent bridges designed to mechanically restrain neighboring anchors in varying orientations to allow fixation to deformed or rotated spine potentially through a series of ball and socket joints.

The apparatus may be attached to the operating table (table fixation) for additional anatomy-to-table stabilization.

In some embodiments, the apparatus may be attached to a soft tissue retractor system for further stabilization.

The apparatus may serve as a patient attachment for navigation reference and/or for a robotic system. The apparatus may also include reusable instruments and/or sterile disposable instruments.

In some embodiments, the apparatus may contain force/torque sensors that can be used by a navigation system or a robotic system to refine mechanical positioning or position indication or to generate an alert upon detection of excessive motion and/or force.

Turning first to FIG. 1, a block diagram of a system 100 according to at least one embodiment of the present disclosure is shown. The system 100 may be used, for example, to carry out a surgical procedure, to detect objects (including, for example, one or more tracking markers on one or more anchors) in a volume of interest, to update a surgical plan based on one or more detected objects, to execute a surgical plan, to carry out one or more steps or other aspects of one or more of the methods disclosed herein, and/or for any other useful purpose. The system 100 comprises a computing device 102, one or more sensors 132, a robot 136, a navigation system 144, a database 148, and a cloud 152. Notwithstanding the foregoing, systems according to other embodiments of the present disclosure may omit any one or more of the one or more sensors 132, the robot 136, the navigation system 144, the database 148, and/or the cloud 152.

The computing device 102 comprises a processor 104, a communication interface 108, a user interface 112, and a memory 116. A computing device according to other embodiments of the present disclosure may omit one or both of the communication interface 108 and the user interface 112.

The processor 104 of the computing device 102 may be any processor described herein or any similar processor. The processor 104 may be configured to execute instructions stored in the memory 116, which instructions may cause the processor 104 to carry out one or more computing steps utilizing or based on data received, for example, from the sensor 132, the robot 136, the navigation system 144, the database 148, and/or the cloud 152.

The computing device 102 may also comprise a communication interface 108. The communication interface 108 may be used for receiving image or other data or other information from an external source (such as the sensor 132, the robot 136, the navigation system 144, the database 148, the cloud 152, and/or a portable storage medium (e.g., a USB drive, a DVD, a CD)), and/or for transmitting instructions, images, or other information to an external system or device (e.g., another computing device 102, the sensor 132, the robot 136, the navigation system 144, the database 148, the cloud 152, and/or a portable storage medium (e.g., a USB drive, a DVD, a CD)). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, RF, GSM, LTE, and so forth). In some embodiments, the communication interface 108 may be useful for enabling the device 102 to communicate with one or more other processors 104 or computing devices 102, whether to reduce the time needed to accomplish a computing-intensive task or for any other reason.

The user interface 112 may be or comprise a keyboard, mouse, trackball, monitor, television, touchscreen, button, joystick, switch, lever, and/or any other device for receiving information from a user and/or for providing information to a user of the computing device 102. The user interface 112 may be used, for example, to receive a user selection or other user input in connection with any step of any method described herein; to receive a user selection or other user input regarding one or more configurable settings of the computing device 102 and/or of another component of the system 100; to receive a user selection or other user input regarding a desired movement of the robot 136; and/or to receive a user selection or other user input regarding a surgical objective; to receive a user selection or other user input regarding a modification to a surgical plan. Notwithstanding the inclusion of the user interface 112 in the system 100, the system 100 may automatically (e.g., without any input via the user interface 112 or otherwise) carry out one or more, or all, of the steps of any method described herein.

Although the user interface 112 is shown as part of the computing device 102, in some embodiments, the computing device 102 may utilize a user interface 112 that is housed separately from one or more remaining components of the computing device 102. In some embodiments, the user interface 112 may be located proximate one or more other components of the system 100, while in other embodiments, the user interface 112 may be located remotely from one or more components of the system 100.

The memory 116 may be or comprise a hard drive, RAM, DRAM, SDRAM, other solid-state memory, any memory described herein, or any other tangible non-transitory memory for storing computer-readable data and/or instructions. The memory 116 may store instructions 120, and/or any other information or data, useful for completing, for example, any step of the method 800 described herein. The memory 116 may store, one or more algorithms 124 (including, for example, a tracking marker detection algorithm, a feature recognition algorithm, an image processing algorithm) and/or one or more surgical plans 128 (each of which may be or comprise, for example, one or more models or other three-dimensional images of a portion of an anatomy of a patient). The instructions 120 and algorithms 124 may, in some embodiments, be organized into one or more applications, modules, packages, layers, or engines, and may cause the processor 104 to manipulate data stored in the memory 116 and/or received from another component of the system 100.

The sensor 132 may be any sensor suitable for obtaining information about a surgical environment and/or about one or more objects (e.g., one or more anchors, anatomical features to which such anchors are attached, and/or bridges) in a working volume or other volume of interest. The sensor 132 may be or comprise, for example, a camera (including a visible light/optical camera, an infrared camera, a depth camera, or any other type of camera); a proximity sensor; and Doppler device; one or more lasers; a LIDAR device (e.g., a light detection and ranging device, and/or a laser imaging, detection, and ranging device); a scanner, such as a CT scanner, a magnetic resonance imaging (MM) scanner, or an optical coherence tomography (OCT) scanner; an O-arm (including, for example, an O-arm 2D long film scanner), C-arm, G-arm, or other device utilizing X-ray-based imaging (e.g., a fluoroscope or other X-ray machine); sensors used for segmental tracking of the spine or of spinal elements; sensors used for vertebrae/implant location detection; an ultrasound probe; or any other imaging device suitable for obtaining images of a work volume or volume of interest. The sensor 132 may be operable to image one or more objects positioned within, proximate, or otherwise around the anatomical features of a patient. The sensor 132 may be capable of taking a 2D image or a 3D image to yield image data. "Image data" as used herein refers to the data generated or captured by an imaging device, including in a machine-readable form, a graphical form, and in any other form. In some embodiments, the sensor 132 may be capable of taking a plurality of 2D images from a plurality of angles or points of view, and of generating a 3D image by combining or otherwise manipulating the plurality of 2D images. In some embodiments, the system 100 may operate without the use of the sensor 132.

The sensor 132 may be operable to image a work volume or volume of interest in real-time (e.g., to generate a video feed or live stream). In such embodiments, the sensor 132 may continuously provide updated images and/or updated image data to the computing device 102, which may continuously process the updated images and/or updated image data as described herein in connection with the method 800. In some embodiments, the sensor 132 may comprise more than one sensor 132.

The sensor 132 may be configured to capture information at a single point in time (e.g., to capture a still image or snapshot at a point in time), or to capture information in real time (e.g., to capture video information and/or a live stream of sensed information). The sensor 132 may be located in or proximate a surgical environment, and positioned so as to be able to detect a surgical working field or volume of interest. The sensor 132 may be, for example, mounted on a robotic arm such as the robotic arm 140, attached to a navigation camera (e.g., of a navigation system 144), or otherwise positioned.

The robot 136 may be any surgical robot or surgical robotic system. The robot 136 may be or comprise, for example, the Mazor X™ Stealth Edition robotic guidance system. The robot 136 may comprise one or more robotic arms 140. In some embodiments, the robotic arm 140 may comprise a first robotic arm and a second robotic arm. In other embodiments, the robot 126 may comprise one robotic arm, two robotic arms, or more than two robotic arms. The robotic arm 140 may, in some embodiments, hold or otherwise support the sensor 132. The robotic arm 140 may, in some embodiments, assist with a surgical procedure (e.g., by holding a tool in a desired trajectory or pose and/or supporting the weight of a tool while a surgeon or other user operates the tool, or otherwise) and/or automatically carry out a surgical procedure. In some embodiments, the system 100 may operate without the use of the robot 136.

The navigation system 144 may provide navigation for a surgeon and/or a surgical robot during an operation. The navigation system 144 may be any now-known or future-developed navigation system, including, for example, the Medtronic StealthStation™ S8 surgical navigation system. The navigation system 144 may include a camera or other sensor(s) for tracking one or more reference markers, navigated trackers, or other objects within an operating room or other room where a surgical procedure takes place. In various embodiments, the navigation system 144 may be used to track a position of the sensor 132 (or, more particularly, of a navigated tracker attached, directly or indirectly, in fixed relation to the sensor 132), and/or of the robot 136 (or one or more robotic arms 140 of the robot 136), and/or of any other object in a surgical environment. The navigation system 144 may include a display for displaying one or more images from an external source (e.g., the computing device 102, sensor 132, or other source) or a video stream from the camera or other sensor of the navigation system 144. In some embodiments, the system 100 may operate without the use of the navigation system 144.

In some embodiments, one or more tracking or reference markers (i.e., markers detectable by the sensor 132 and/or by the navigation system 144) may be placed on the robot 136, the robotic arm 140, an anchor or bridge as described herein, or any other object in the surgical space. The reference markers may be tracked by the navigation system 144, and the results of the tracking may be used by the robot 136 and/or by an operator of the system 100 or any component thereof. In some embodiments, the navigation system 144 can be used to track other components of the system 100 (e.g., the sensor 132) and the system can operate without the use of the robot 136 (e.g., with a surgeon manually manipulating, based on guidance from the navigation system 144, any object useful for carrying out a surgical procedure).

The database 148 may store image data generated by one or more sensors 132 and may be configured to provide such image data (e.g., electronically) to the computing device 102 (e.g., for display on or via a user interface 112, or for use by the processor 104 in connection with any method described herein) or to any other device, whether directly or via the cloud 152. In some embodiments, the database 148 may be or comprise part of a hospital image storage system, such as a picture archiving and communication system (PACS), a health information system (HIS), and/or another system for collecting, storing, managing, and/or transmitting electronic medical records including image data. The database 148 may store any of the same information stored in the memory 116 and/or any similar information. In some embodiments, the database 148 may contain a backup or archival copy of information stored in the memory 116.

The cloud 152 may be or represent the Internet or any other wide area network. The computing device 102 may be connected to the cloud 152 via the communication interface 108, using a wired connection, a wireless connection, or both. In some embodiments, the computing device 102 may communicate with the database 148 and/or an external device (e.g., a computing device) via the cloud 152.

Figure 3:
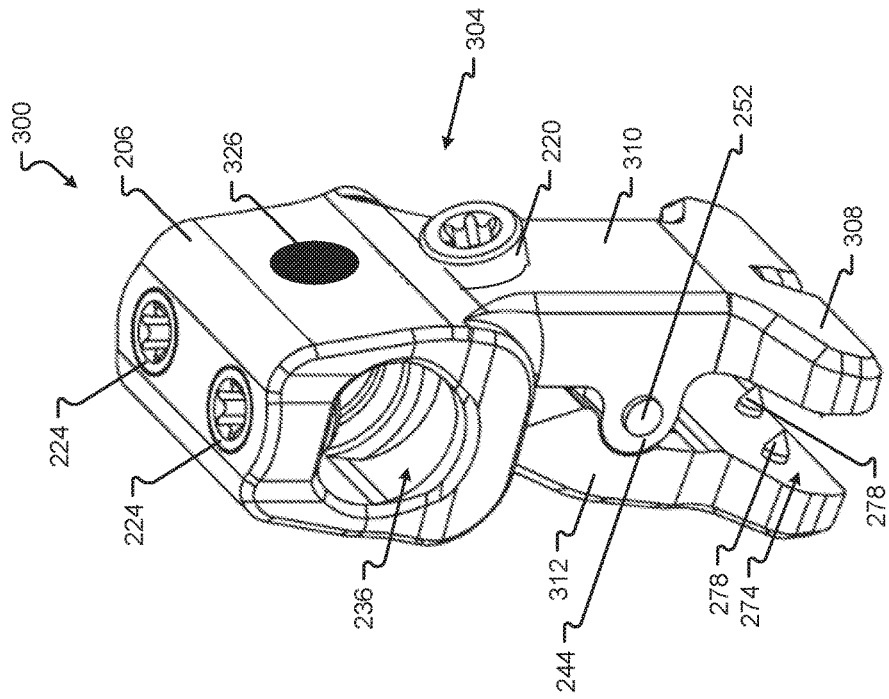
FIG. 3 depicts an anchor according to at least one embodiment of the present disclosure.
Figure 2:
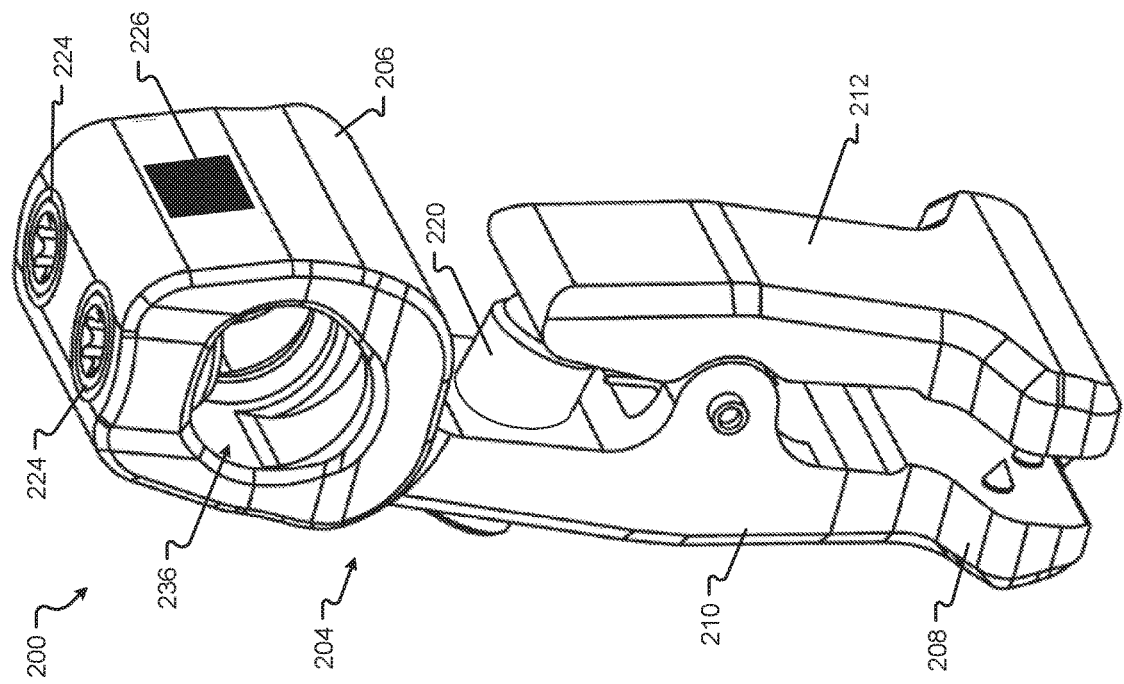
FIG. 2 depicts an anchor according to at least one embodiment of the present disclosure.
Figure 4:
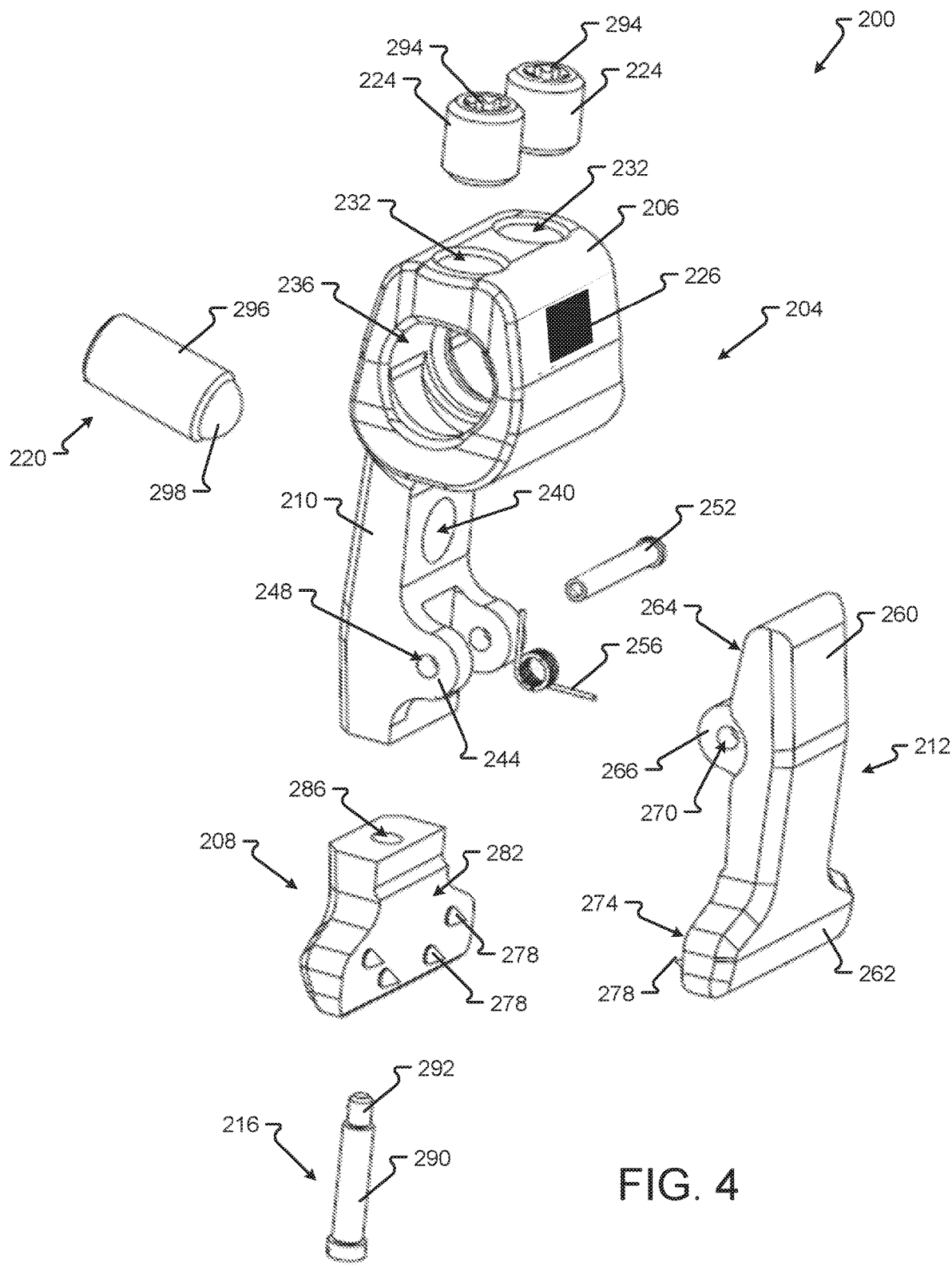
FIG. 4 is an exploded view of the anchor of FIG. 2.

Turning now to FIGS. 2-4, an anchor 200 and an anchor 300 according to embodiments of the present disclosure will be described. The anchor 200 and the anchor 300 are substantially similar to each other, although the anchor 200 is taller than the anchor 300, which in turn is shorter than the anchor 200. Each anchor 200 and 300 may be made of metal, a metal alloy, plastic, polyetheretherketone (PEEK), any biocompatible material, and/or any combination of any of the foregoing.

The anchor 200 comprises a body 204 with a head 206 and an arm 210. The body 204 may be integrally fashioned of a single piece of a material, or may comprise an assembly of multiple components (e.g., the head 206 may be fashioned separately from and subsequently attached to the arm 210). The anchor 200 further comprises a rotatable foot 208, an arm 212, a locking screw 220, a plurality of bridge interface set screws 224, and a bridge interface or receptacle 236.

The head 206 comprises a tracking marker 226, which may be provided directly on the head 206 or attached to the head 206. The tracking marker 226 may be or comprise a geometric shape (as here, where the tracking marker 226 comprises a square), a geometric pattern (such as, for example, a UPC or QR code), one or more specific contours, one or more colors, one or more reflective spheres, one or more LEDs, or any other marker detectable by a sensor (e.g., a sensor 132 and/or a sensor of a navigation system 144) that may be used to determine a pose (e.g., position and orientation) of the anchor 200. The tracking marker 226 may be an optical tracking marker or an electromagnetic tracking marker. In some embodiments, such as with the anchors 200 or 300 illustrated in FIGS. 2 and 3, the tracking marker 226 or 326 may be passive and unpowered. In other embodiments, the tracking marker 226 or 326 may be active and powered, for example using a battery provided in the body 204 or 304 or elsewhere in the anchor 200 or 300, respectively.

The head 206 also comprises one or more bridge interfaces or receptacles 236, and a corresponding number of set screw apertures 232. In the embodiment illustrated in FIG. 4, the head 206 comprises two bridge interfaces 236, positioned on opposite sides of the head 206, and two set screw apertures 232. The set screw apertures 232 extend from an upper surface of the head 206 into the bridge interfaces 236, although in other embodiments the set screw apertures 232 may extend through a different surface of the head 206 into the bridge interfaces 236.

The set screw apertures 232 are adapted to receive set screws 224, which may be tightened against a bridge that extends into the bridge receptacle to prevent movement of the bridge relative to the anchor 200. The set screw apertures 232 may comprise internal threads, and the set screws 224 may comprise external threads, such that the set screws 224 are configured to threadingly engage the set screw apertures 232. Each set screw may comprise a drive 294 engageable by a tool (e.g., a screwdriver) to tighten and/or loosen the set screw 224 within the set screw aperture 232.

In some embodiments, other mechanisms for locking a bridge in position relative to the anchor 200 may be used. For example, in some embodiments, the head 206 may comprise a slot extending therethrough, with one or more bolts, screws, or other fasteners engaging the head 206 and configured to adjust a width of the slot. In such embodiments, the slot may be opened (e.g., the width of the slot may be increased) to receive a bridge in the bridge interface 236, after which the bolt(s), screw(s), or other fastener(s) used to adjust the width of the slot may be tightened to narrow or close the slot and cause the head 206 to tightly grip the portion of the bridge within the bridge interface 236.

The bridge interfaces 236 of some anchors according to embodiments of the present disclosure may comprise one or more sensors configured to detected a position of a bridge within the bridge interface. For example, in some embodiments, an anchor interface of a bridge may be provided with a magnet, and a bridge interface of an anchor may comprise a magnetic sensor configured to detect a magnetic field. A wired or wireless interface may be used to transmit information from the magnetic sensor to, for example, a processor 104 of a computing device 102 for determination of a position of the bridge within the bridge interface of the anchor. Such information may be used, for example, to confirm or update a surgical plan, or in connection with generation or verification of a model of a patient anatomy, or for any other useful purpose.

The body 204 further comprises an arm 210. The arm 210 extends from the head 206 and comprises at least one extension 244 comprises an aperture 248 for receiving a pin 252. The at least one extension 244 may have a rounded outer surface to facilitate rotational movement of the arm 212 (described in more detail below) relative to the arm 210. In other embodiments, however, the at least one extension 244 may have an outer surface without a rounded shape. As shown in FIG. 4, the arm 210 includes two extensions 244, extending parallel to each other from opposite sides of the arm 210, such that the apertures 248 thereof are coaxial and able to receive the pin 252.

The pin 252 may be made of metal, a metal alloy, plastic, PEEK, or any other material suitable for securing the arm 212 to the arm 210 and for withstanding the forces exerted thereon during use of the anchor 200. The pin 252 may comprise a flange on one end thereof to stop the pin 252 from passing all the way through the aperture(s) 248. Some or all of the pin 252 and one or more of the apertures 248 may be threaded to reduce a chance of the pin 252 falling out of the apertures 248 and thus disconnecting the arm 210 from the arm 212. In other embodiments, the pin 252 may comprise a hole extending from an end thereof into which a locking pin may be inserted after the pin 252 has been inserted through the apertures 248. In still other embodiments, once the pin 252 has been inserted into the apertures 248, the previously un-flanged end of the pin 252 may be flanged to prevent the pin from moving axially within the apertures 248.

A rotatable foot 208 is rotatably mounted to the arm 210 using a pin 216. The pin 216 may comprise a smooth portion 290 around which the foot 208 is rotatable, and a threaded portion 292 that is configured to engage a corresponding threaded aperture within the arm 210 so as to secure the pin 216, and the foot 208, to the arm 210. The pin 216 also comprises a flanged end to prevent the foot 208 from falling off of the pin 216 once secured to the arm 210. The foot 208 is rotatably mounted to the arm 210 to enable the foot 208 to rotate as necessary to best engage an anatomical feature to which the anchor 200 is clamped.

The foot 208 comprises an aperture 286 extending therethrough and configured to receive the pin 216. The foot 208 also comprises a contact surface 282, from which a plurality of teeth 278 or other non-slip, grip-enhancing features extend. The contact surface 282 may be planar in some embodiments, as shown in FIG. 4, while in other embodiments the contact surface 282 may be ridged or otherwise provided with integral grip-enhancing features. The contact surface may simply be an integral surface of the foot 208, or the contact surface may be or comprise a plating or other cover attached to the foot 208 using glue or other adhesive, one or more mechanical fasteners (whether the teeth 278 or otherwise), or some other attachment method. In embodiments where the anchor 208 is sterilizable and reusable, the contact surface 282 (and, in some embodiments, the teeth 278) may be removable and disposable, and configured to be replaced after each use.

A foot 208 as described herein may have a width adapted to engage only a single anatomical element (e.g., a spinous process of a single vertebra), or a width adapted to engage a plurality of anatomical elements simultaneously (e.g., a spinous process of multiple adjacent vertebrae).

The teeth 278 may be made of the same material or a different material than the remaining portions of the foot 208. The teeth 278 may be manufactured separately from one or more other portions of the foot 208, or may be integrally fashioned as part of the foot 208 from a single piece of material. The teeth 278 may be permanently or removably installed in the foot 208. The teeth 278 are configured to engage an anatomical feature to which the anchor 200 is clamped and prevent movement of the anchor 200 relative to the anatomical feature. To accomplish such engagement, the teeth 278 may comprise one or more points, ridges, serrations, non-slip surfaces, or other features for grabbing, gripping, engaging, or otherwise maintaining a secure attachment to the anatomical feature in question.

The anchor 200 further comprises an arm 212, which comprises an elongate lever 260 and a foot 262. An extension 266, which may be the same as or similar to the extension 244 described above, extends from the lever 260. An aperture 270 within the extension 266 receives the pin 252 when the anchor 200 is assembled, and enables the lever 260 to rotate around the pin 252 (which therefore acts as a fulcrum for the arm 212).

The foot 262 of the arm 212 comprises a contact surface 274, which may be the same as or similar to the contact surface 282 of the foot 208. The foot 262 also comprises one or more teeth 278, which are described above. The foot 208 and the foot 262 together engage an anatomical feature to which the anchor 200 is attached.

When the anchor 200 is assembled, the aperture 270 is aligned with the apertures 248 as well as an opening in the spring 256, and the pin is then inserted through the apertures 248, the aperture 270, and the spring 256. The spring 256 biases the clamp of the anchor 200 (comprising the arm 210, the arm 212, the foot 208, and the foot 262) toward a fully closed position. In other words, the spring 256 biases the contact surface 282 toward the contact surface 274, thus generating a clamp force that helps to secure the anchor 200 to an anatomical feature. The embodiment of FIG. 4 utilizes a torsional spring 256, but other embodiments may utilize other types of springs, configured as needed to bias the clamp of the anchor 200 into the closed position.

The anchor 200 also comprises a locking screw 220, which comprises a threaded shaft 296 and an engagement head 298. The threaded shaft 296 is adapted to be received by an internally threaded aperture 240 on the arm 210, and the engagement head 298 is configured to press against the surface 264 of the lever 260. As a result, by threading the locking screw 220 into the aperture 240 until the engagement head 296 contacts the surface 264, the arm 212 can be prevented from rotating counterclockwise (e.g., to move the clamp of the anchor 200 into a fully open position, with the contact surfaces 274 and 282 separated by a maximum possible distance, given the other components of the anchor 200). Moreover, by continuing to thread the locking screw 220 farther into the aperture 240 after the engagement head 296 makes contact with the surface 264, the lever 260 may be forcibly rotated clockwise, thus increasing the clamp force exerted by the contact surfaces 274 and 282 on an anatomical feature (and increasing the effectiveness of the teeth 278, which will more securely engage the anatomical feature as the clamping force increases. If no anatomical feature is positioned between the contact surfaces 274 and 282, then the clamp may be moved to (and locked in) a fully closed position, in which the contact surfaces 274 and 282 are separated by a minimum possible distance (given the protrusion therefrom of the teeth 278). To reduce the clamping force or release the clamp of the anchor 200 from the anatomical feature altogether, the locking screw 220 may unthreaded from the aperture 240, thus enabling the arm 212 to be rotated in the counterclockwise direction around the pin 252 so as to move the contact surface 274 farther away from the contact surface 282, with the effect of disengaging an anatomical feature gripped by the clamp.

The anchor 300 comprises a body 304, a rotatable foot 308, and an arm 312. The anchor 300 also shares a number of features with the anchor 200, which features are commonly numbered and described above.

The body 304 is substantially similar to the body 204 as described above. The head 206 is identical to the head 206 of the anchor 200 described above, but for a different tracking marker 326, which allows the anchor 300 to be distinguished from the anchor 200 by a navigation system 144 or sensor 132 in a surgical setting. The arm 310 the shorter than the arm 210, but comprises all of the same features of the arm 210 described above.

Similarly, the arm 312 is shorter than the arm 212, but comprises all of the same features of the arm 212 described above. So too with the foot 308, which is shaped differently than the foot 208 but comprises all of the same features of the foot 208 described above.

In addition to encompassing anchors of different heights, the present disclosure also encompasses embodiments comprising anchors of different sizes and dimensions (e.g., different widths, lengths, cross-sectional areas, contact surface area).

Anchors according to some embodiments of the present disclosure may have a height of less than five centimeters (cm), or between five and eight cm, or between eight and ten cm, or between nine and eleven cm, or less than ten cm, or greater than or equal to ten cm. Bridges according to embodiments of the present disclosure may have a length of more than one cm, or between one and five cm, or between five and ten cm, or between eight and twelve cm, or less than ten cm, or greater than or equal to ten cm.

The anchor 300 may be used and operated in the same manner as, or in a substantially similar manner to, the anchor 200.

In some embodiments of the present disclosure, an anchor may comprise a head 206 secured to the shaft of a Shanz screw. Such anchors may be threaded into an anatomical feature (e.g., a pelvis, a vertebra) of a patient to secure the anchor to the anatomical feature, after which a one or more bridges may be connected to the head 206 as described elsewhere herein.

Figure 5:
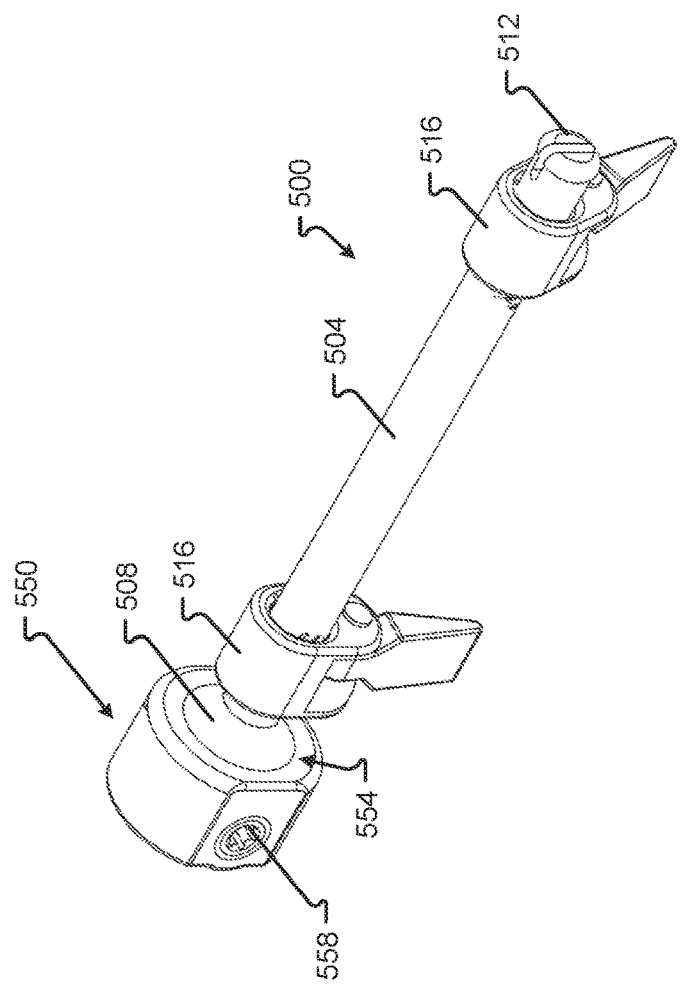
FIG. 5 depicts a bridge and an adaptor according to at least one embodiment of the present disclosure.

Turning now to FIG. 5, a bridge 500 may be used to secure an anchor such as the anchor 200 or 300 (and thus the anatomical element(s) to which the anchor is secured) to an operating table, a robot, or another structure (e.g., a wall, ceiling, floor) via an adaptor 550. Use of an adaptor 550 to so secure an anchor in this manner beneficially enables movement of the anatomical elements in question, relative to the operating table, robot, or other structure to which the adaptor 500 is connected, to be restrained or entirely prevented.

The bridge 500 comprises a rigid, elongate member 504 having a first end with a first anchor interface 508 and a second end with a second anchor interface 512. The elongate member 504 may be made of any material described herein and may in some embodiments be manufactured of a radiolucent material. The rigid, elongate member may comprise a core material extending along an axis thereof and having a first rigidity, and an outer material surrounding the core material and having a second rigidity different than the first rigidity. Although shown as having a circular cross-section, the rigid, elongate member may in some embodiments comprise a non-circular cross-section, which may be, for example, a square cross-section, a rectangular cross-section, a triangular cross-section, a star-shaped cross-section, or any other cross-sectional shape.

The first anchor interface 508 is a ball, and is received by a bridge interface 554 of the adaptor 550, which bridge interface 554 is in the form of a socket. The bridge interface 554 may be made of the same material as or a different material than the ball of the first anchor interface 508, and may be designed to have some flexibility or play that enables a portion of the bridge interface 554 to give way as the ball of the first anchor interface 508 is inserted into the bridge interface 554, and then to spring back into position to help secure the ball of the first anchor interface 508 within the bridge interface 554. Use of a ball and socket as shown beneficially enables the bridge 500 to be positioned in any one of a plurality of possible positions relative to the adaptor 550, as needed. Once the bridge 500 is properly positioned, the set screw 558 may be tightened against the anchor interface 508 of the bridge 500.

The second anchor interface 512 of the bridge 500 comprises a different type of interface than the first anchor interface 508. Specifically, the second anchor interface 512 comprises a slotted cylinder with a rounded flange extending from an end thereof. The two halves of the second anchor interface 512 (separated by the slot) are configured to bend toward each other when pressed into a corresponding bridge interface (e.g., on an anchor such as the anchor 200 or 300), and then to spring back into position to prevent the second anchor interface 512 from falling out of or being easily removed from the corresponding bridge interface. A set screw such as the set screws 224 and 558 may be used to further secure the second anchor interface 512 into a corresponding bridge interface. Although the second anchor interface 512 is not configured to allow positioning of the bridge 500 at a variety of angles relative to the corresponding bridge interface, the second anchor interface 512 may permit rotation of the bridge 500 about an axis thereof relative to the corresponding bridge interface, which may be beneficial in some instances, including in particular in connection with a rotatable fixation bridge as described in U.S. Patent Application No. 63/044,535, entitled "Rotatable Fixation Bridge" and filed on Jun. 26, 2020, the entirety of which is hereby incorporated by reference herein.

The rigid, elongate member 504 may support one or more attachments 516, which may be used to maintain spacing between the elongate member 504 and one or more anatomical elements or other objects, or to support a surgical instrument or tool, or for any other useful purpose.

Figure 6:
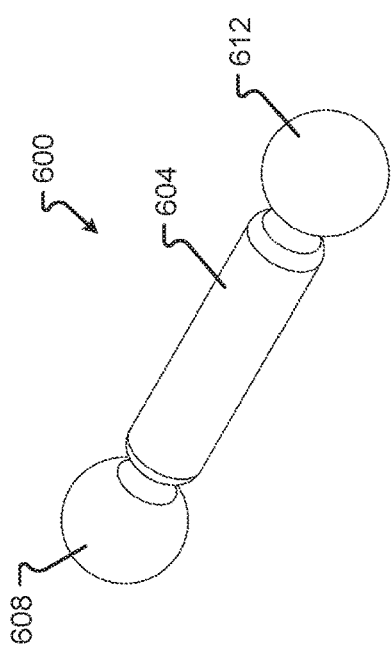
FIG. 6 depicts a bridge according to at least one embodiment of the present disclosure.
Figure 7:
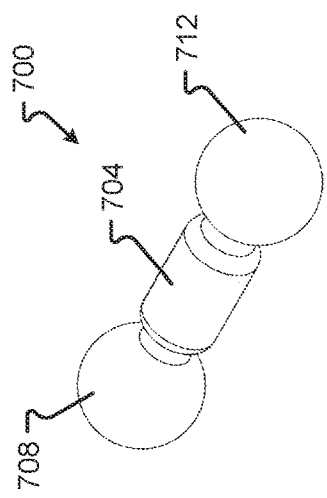
FIG. 7 depicts a bridge according to at least one embodiment of the present disclosure.

With reference to FIGS. 6 and 7, two bridges—a longer bridge 600 and a shorter bridge 700—are illustrated. The bridges 600 and 700 are identical but for the rigid, elongate member 604 of the bridge 600 having a greater length than the rigid, elongate member 704 of the bridge 700. Unlike the bridge 500, the bridges 600 and 700 each comprise identical anchor interfaces at each end thereof—anchor interfaces 608 and 612 on the bridge 600 and anchor interfaces 708 and 712 on the bridge 700. These anchor interfaces are all balls, configured to be received in corresponding sockets such as the bridge interface 236 described above in connection with the anchors 200 and 300. However, other anchor interfaces (useful, for example, for joints other than ball-and-socket joints) may be used in embodiments of the present disclosure. Moreover, in some embodiments of the present disclosure that do use ball-and-socket joints, the bridge may comprise the socket(s), and the anchor(s) and/or adaptor(s) may comprise the ball(s).

Although the bridges 600 and 700 are described has being identical but for their different lengths, in some embodiments, two or more bridges used in a stabilization system according to embodiments of the present disclosure may comprise one or more differences. For example, the elongate member 704 of a shorter bridge 700 may have a smaller cross-sectional area than an elongate member 604 of a longer bridge 600, because the same rigidity may be achieved with less structure to the shorter length of the bridge 700. Additionally, the elongate members of different bridges may have different cross-sectional shapes; each bridge may comprise only one, or more than two, anchor interfaces; and each bridge may comprise two or more different kinds of anchor interfaces. Although the elongate members of the bridges described herein are all straight, in some embodiments the elongate members may be curved or otherwise non-linearly shaped.

In some embodiments, some or all of the bridges 600 or 700 may be manufactured of photoelastic material, from which a strain imposed on the bridge 600 or 700 or portion thereof may be determined by illuminating the photoelastic material with a particular light. In such embodiments, a sensor 132 as described above may be configured to illuminate the photoelastic material with the light in question and to detect a color, a reflective frequency, and/or another characteristic of the photoelastic material when so illuminated. A processor such as the processor 104 described above may then be used to calculate a strain imposed on the bridge 600 or 700, which strain may then be displayed to a surgeon or other user, or used for one or more calculations regarding a needed surgical procedure or step thereof, or used to make one or more recommendations to the surgeon or other user, whether regarding the spinal stabilization system that comprises the bridge, or regarding a surgical plan, or otherwise regarding the patient.

Stabilization systems according to embodiments of the present disclosure may comprise a plurality of anchors such as the anchors 200 and/or 300, a plurality of bridges such as the bridges 500, 600, and/or 700, and in some embodiments one or more adaptors 550. In use, an anchor such as the anchor 200 or 300 may be affixed to one or more anatomical features (e.g. one or more vertebrae, or more specifically the spinous process of one or more vertebrae), using the clamp formed by the arms 210 and 212 or 310 and 312 thereof. One or more bridges, as appropriate, may then be connected to the anchors (e.g., by inserting the anchor interface(s) of each bridge into the bridge interface(s) of each anchor, and/or vice versa). Once the system is generally positioned relatively to the corresponding anatomical features, the anchors may be locked in place by tightening the locking screw thereof, thus forcing the contact surfaces of the anchors closer to each other, increasing a clamping or squeezing force on the anatomical feature, and improving the engagement of the teeth of the anchors with the anatomical feature. Additionally, the bridges may be locked into place by tightening the set screws or other locking features of the bridge receptacles of the anchors. With the anchors and bridges locked into place, relative movement of the anatomical features to which the anchors are secured will be partially if not entirely prevented.

The use of anchors 200 and 300 having different heights, and of bridges 500, 600, and/or 700 having different lengths, beneficially enables a surgeon or other user of a stabilization system as described herein to select and use components that match the elevations and distances of the particular anatomical features of a given patient. A pediatric patient, for example, may require shorter bridges such as the bridge 700, while an adult patient may require longer bridges such as the bridge 600. Moreover, longer or shorter bridges may be required depending on the distance between anatomical features to which the anchors of the stabilization system are secured.

In some embodiments, one or more anchors such as the anchors 200 and 300 of a stabilization system may be secured to one or more anatomical features, without the use of any bridges. In such embodiments, the purpose of the anchors may not be to prevent motion of the anatomical feature(s) to which they are connected, but rather to enable detection of such motion. In such embodiments, an initial position of each anchor (once each anchor is connected to one or more anatomical features) may be determined based on detection of a tracking marker (e.g., a tracking marker 226 or 326 thereof). Subsequent positions of each anchor may then be determined in a similar manner, and compared to a previously determined position of each anchor to determine a movement of each anchor during the intervening time period.

Figure 8:
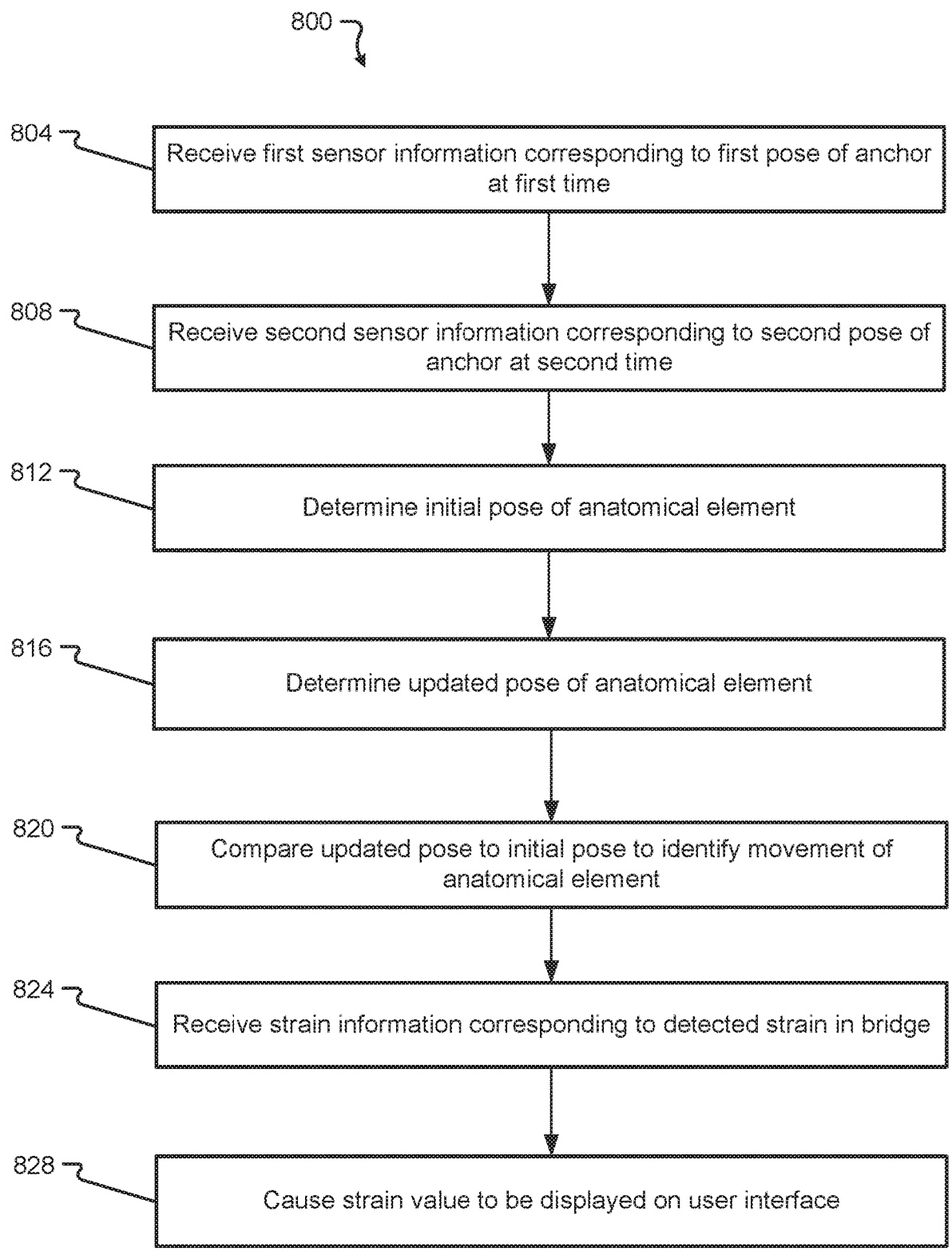
FIG. 8 is a flowchart of a method according to at least one embodiment of the present disclosure.

Turning now to FIG. 8, a method 800 according to at least one embodiment of the present disclosure may be used to determine movement of one or more anatomical features and/or to determine a strain in a stabilization system as described herein. The method 800 may beneficially enable a surgeon to determine whether a registration is still valid; and/or to update a registration, an anatomical model, or a surgical plan; and/or to identify and remediate a potential negative impact to patient safety. The method 800 may be executed by a processor, for example a processor 104, and may utilize one or more components of a system such as the system 100.

The method 800 comprises receiving first sensor information corresponding to a first pose of an anchor at a first time (step 804). The first sensor information may be received, for example, from a sensor 132 or from a navigation system 144. The first sensor information may be or comprise information about a detected tracking marker (such as a tracking marker 226 or 326) of an anchor (such as an anchor 200 or 300). The first sensor information may be raw or processed data. In some embodiments, the first sensor information may be information input into a tracking marker detection algorithm (so as to detect a tracking marker, and based upon which a pose of the anchor may be determined), or information output by a tracking marker detection algorithm (comprising a determined pose of the tracking marker and thus of the anchor). The first sensor information may comprise sufficient information from which to determine a pose of the anchor, although in some embodiments additional information (such as, for example, information about a position of a tracking marker relative to an anchor on which the tracking marker is positioned) may be needed to determine a pose of the anchor.

The first sensor information may be received directly from a sensor 132 or a navigation system 144, or may be received from or via a database 148, a network such as the cloud 152, or any other component or system. The first sensor information may, in some embodiments, comprise information obtained from one or more sensors as well as additional information obtained or received from, for example, a memory such as the memory 116, or a database such as the database 148.

The first time may be a time at which some or all of the first sensor information is obtained. The first time may also be or correspond to a time at which one or more registration images are obtained, such that the first pose of the anchor corresponds to a position of the anchor during a registration procedure.

The method 800 also comprises receiving second sensor information corresponding to a second pose of an anchor at a second time (step 808). The step 808 may be substantially the same as the step 804, but for the second time being after the first time. The second pose may be the same as the first pose or different than the first pose.

The method 800 also comprises determining an initial pose of an anatomical element (step 812). The anatomical element is an anatomical element to which the anchor is secured. In some embodiments, the determining may comprise determining an initial pose of the anchor based on the first sensor information, based upon which determined initial pose of the anchor an initial pose of the anatomical feature may be determined. In such embodiments, additional information may be obtained and utilized in the determination (including, for example, information about a relative position of the anchor to the anatomical feature, which may be obtained from a surgical plan, or from a memory such as the memory 116, or from a database such as the database 148). In other embodiments, the first sensor information may comprise an initial pose of the anchor, and the initial pose of the anatomical feature may be determined based upon the first sensor information without first calculating or otherwise determining an initial pose of the anchor. In still other embodiments, the initial pose of the anatomical feature may simply be determined to be or assigned to be the initial pose of the anchor. Thus, for example, in embodiments where the first time corresponds to a time at which a registration process was conducted or completed, and the purpose of the method 800 is to determine whether an anatomical feature has moved since the registration process, any movement of the anchor may be considered a proxy for any movement of the anatomical feature, such that the actual pose of the anatomical feature need not be determined, but the anatomical feature may nevertheless be assigned an initial pose to use for future comparisons and movement determinations. In such embodiments, for ease of calculation, the assigned initial pose may simply be the initial pose of the anchor.

The method 800 also comprises determining an updated pose of the anatomical element (step 816). Determining the updated pose of the anatomical element may be completed in the same manner as, or in a substantially similar manner to, the determining the initial pose of the anatomical element in the step 812, except that the determining the updated pose of the anatomical element is based on the second sensor information and/or the second pose of the anchor rather than the first sensor information and/or the first pose of the anchor.

The method 800 also comprises comparing the updated pose of the anatomical element to the initial pose of the anatomical element to identify any movement of the anatomical element (step 820). The comparing may comprise utilizing one or more algorithms such as the algorithms 124, including one or more image processing algorithms, feature recognition algorithms, or other algorithms. Where the first sensor information and the second sensor information comprise images or other image data, the images may be overlaid on one another such that common features are aligned with one another, and the initial and updated poses of the anatomical element (and/or of the anchors, as appropriate) may be examined to determine if they are the same. Alternatively, the comparing may comprise simply comparing one or more numbers or other parameters describing the initial pose to one or more numbers or other parameters describing the second pose, and evaluating whether the numbers are the same or different. Where the result of the comparison is a determination that the pose of the anatomical element has not changed, then no further action may be taken. Where the result of the comparison is a determination that the pose of the anatomical element has changed, then a recommendation may be made to a surgeon or other user (e.g., via a user interface such as the user interface 112) that a registration process should be repeated, or a surgical model may be updated to reflect the new pose of the anatomical element, or any other appropriate step may be taken.

In some embodiments, the method 800 also comprises receiving strain information corresponding to detected strain in a bridge (e.g., a bridge connecting two anchors, or an anchor and an adaptor, as described herein) (step 824). The strain information may be or comprise raw or processed data from a sensor such as the sensor 132 (which may be, for example, a polariscope) regarding a detected strain in the bridge. For example, where the bridge is made entirely or partially of photoelastic material, the strain information may comprise information about a birefringence of the photoelastic material, and/or about one or more other characteristics of the photoelastic material, from which a strain in the bridge may be calculated or otherwise determined.

The method 800 also comprises causing a strain value to be displayed on a user interface (step 828). The strain value may be a value calculated using any known method based on the strain information received in the step 824. In some embodiments, the strain value may be obtained directly from the strain information, without any need for further calculations. The user interface may be, for example, a user interface 112. The strain value may be displayed on the user interface to enable a surgeon to monitor patient safety, to evaluate a planned step of a surgical procedure, to determine whether or how to proceed with a surgical procedure or a step thereof, or to accomplish any other purpose.

Methods according to embodiments of the present disclosure may comprise more or fewer steps than described above in connection with the method 800, and may also comprise one or more different steps than those described above in connection with the method 800. The method 800 may be used in connection with one or more anchors of a stabilization system as described herein, and/or in connection with one or more anchors and bridges of stabilization system as described herein.

The foregoing discussion has been presented for purposes of illustration and description. The foregoing is not intended to limit the disclosure to the form or forms disclosed herein.

In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A spinal stabilization system, comprising:
   a plurality of anchors, each anchor comprising:
      a clamp configured to engage an anatomical element, the clamp movable between a fully open position and a fully closed position, the clamp defined by a first arm and a second arm, the first arm having an internally threaded aperture, the second arm configured to rotate relative to the first arm via a pivot point, the second arm having a lever and a second foot;
      a spring positioned at the pivot point and configured to bias the clamp to the fully closed position;
      a locking screw configured to selectively prevent the clamp from being moved into the fully open position, the locking screw having a threaded shaft and an engagement head, the threaded shaft received by the internally threaded aperture on the first arm, the engagement head configured to press against a surface of the lever of the second arm to prevent the second arm from rotating counterclockwise into the fully open position; and
      a head having two bridge interfaces adjacent to each other,
      wherein the first arm extends from the head to a first foot and the second arm extends from the head to the second foot, each of the first foot and the second foot having a planar surface; and
   at least one bridge comprising a rigid member having a first end and a second end opposite the first end, each of the first end and the second end comprising an anchor interface;
   wherein the bridge interface is configured to receive the anchor interface.

2. The spinal stabilization system of claim 1, wherein a first one of the plurality of anchors has a first height, and a second one of the plurality of anchors has a second height different than the first height.

3. The spinal stabilization system of claim 1, wherein a first one of the plurality of anchors has a first height less than 10 cm, and a second one of the plurality of anchors has a second height greater than or equal to 10 cm.

4. The spinal stabilization system of claim 1, wherein the clamp comprises:
 a first contact surface opposite and facing a second contact surface; and
 a plurality of teeth on at least one of the first contact surface and the second contact surface, the plurality of teeth configured to prevent movement of the clamp relative to the anatomical element when the clamp is engaged with the anatomical element.

5. The spinal stabilization system of claim 1, wherein the anchor interface is a ball, and first bridge interface of the two bridge interfaces is a socket.

6. The spinal stabilization system of claim 1, wherein each bridge interface of the two bridge interfaces further comprises a lock configured to selectively prevent movement of the bridge relative to the anchor when the anchor interface is received by the bridge interface.

7. The spinal stabilization system of claim 1, wherein at least one anchor of the plurality of anchors comprises a tracking marker.

8. The spinal stabilization system of claim 1, wherein the at least one bridge is a plurality of bridges, and a first bridge of the plurality of bridges has a first length different than a second length of a second bridge of the plurality of bridges.

9. An anatomical stabilization system comprising:
 an anchor comprising:
  a clamp for securing the anchor to an anatomical feature and comprising first and second contact surfaces, each having a non-slip feature, the clamp defined by a first arm and a second arm, the first arm having an internally threaded aperture, the second arm configured to rotate relative to the first arm via a pivot point, the second arm having a lever and a second foot;
  a spring positioned at the pivot point and configured to bias the clamp to a fully closed position;
  a lock configurable to prevent release of the clamp from the anatomical feature, the lock having a locking screw with a threaded shaft and an engagement head, the threaded shaft received by the internally threaded aperture on the first arm, the engagement head configured to press against a surface of the lever of the second arm to prevent the second arm from rotating counterclockwise into a fully open position;
  a head having at least two bridge receptacles, each bridge receptacle adjacent to each other; and
  a tracking marker,
  wherein the first arm extends from the head to a first foot and the second arm extends from the head to the second foot, each of the first foot and the second foot having a planar surface.

10. The anatomical stabilization system of claim 9, further comprising:
 a bridge comprising a rigid elongate member with a first end opposite a second end, the first end configured to be received by one bridge receptacle of the two bridge receptacles.

11. The anatomical stabilization system of claim 10, wherein the bridge comprises a photoelastic material.

12. The anatomical stabilization system of claim 10, further comprising a plurality of anchors and a plurality of bridges.

13. The anatomical stabilization system of claim 10, further comprising an adaptor for securing the second end of the bridge to a surgical robot, an operating table, or a bed.

14. The anatomical stabilization system of claim 9, wherein the clamp is configured to be secured to a plurality of anatomical features simultaneously.

15. The anatomical stabilization system of claim 9, wherein the tracking marker is an optical tracking marker or an electromagnetic tracking marker.

16. An anchor comprising:
 a clamp configured to engage an anatomical element, the clamp movable between a fully open position and a fully closed position, the clamp comprising first and second contact surfaces, each having a non-slip feature, the clamp defined by a first arm and a second arm, the first arm having an internally threaded aperture, the second arm configured to rotate relative to the first arm via a pivot point, the second arm having a lever and a second foot;
 a spring positioned at the pivot point and configured to bias the clamp to the fully closed position;
 a locking screw configured to selectively prevent the clamp from being moved into the fully open position, the locking screw having a threaded shaft and an engagement head, the threaded shaft received by the internally threaded aperture on the first arm, the engagement head configured to press against a surface of the lever of the second arm to prevent the second arm from rotating counterclockwise into the fully open position;
 a head having at least two bridge receptacles, wherein each receptacle is adjacent to each other; and
 a tracking marker,
 wherein the first arm extends from the head to a first foot and the second arm extends from the head to the second foot, each of the first foot and the second foot having a planar surface.

17. The anchor of claim 16, wherein the tracking marker is an optical tracking marker or an electromagnetic tracking marker.

18. The anchor of claim 16, wherein the clamp comprises one or more set screw apertures configured to receive a corresponding one or more set screws, wherein the one or more set screws are configured to tighten against a bridge when the bridge is positioned in the at least two bridge receptacles.

* * * * *